US012685442B2

(12) United States Patent
Sinha et al.

(10) Patent No.: US 12,685,442 B2
(45) Date of Patent: Jul. 21, 2026

(54) ULTRASOUND INTRAOCULAR PRESSURE SENSOR IN SCLERA OR IN CORNEA

(71) Applicant: Verily Life Sciences LLC, Dallas, TX (US)

(72) Inventors: Supriyo Sinha, Menlo Park, CA (US); Dimitri T. Azar, Chicago, IL (US)

(73) Assignee: Verily Health Inc., Dallas, TX (US)

( * ) Notice: Subject to any disclaimer, the term of this patent is extended or adjusted under 35 U.S.C. 154(b) by 964 days.

(21) Appl. No.: 17/827,059

(22) Filed: May 27, 2022

(65) Prior Publication Data

US 2022/0378291 A1 Dec. 1, 2022

Related U.S. Application Data

(60) Provisional application No. 63/195,530, filed on Jun. 1, 2021.

(51) Int. Cl.
*A61B 3/16* (2006.01)
*A61B 8/10* (2006.01)

(52) U.S. Cl.
CPC ................ *A61B 3/165* (2013.01); *A61B 8/10* (2013.01)

(58) Field of Classification Search
CPC .............. A61B 3/165; A61B 8/10; A61B 3/16
See application file for complete search history.

(56) References Cited

U.S. PATENT DOCUMENTS

| | | | |
|---|---|---|---|
| 6,432,050 | B1 | 8/2002 | Porat et al. |
| 7,678,065 | B2 | 3/2010 | Haffner et al. |
| 10,687,704 | B2 | 6/2020 | Hastings et al. |
| 2004/0211260 | A1* | 10/2004 | Girmonsky ........... G01L 9/0008 |
| | | | 702/56 |
| 2004/0254438 | A1 | 12/2004 | Chuck et al. |
| 2005/0049499 | A1 | 3/2005 | Kaplan |
| 2005/0119636 | A1* | 6/2005 | Haffner .................... A61B 3/16 |
| | | | 623/4.1 |
| 2011/0160561 | A1 | 6/2011 | Hastings et al. |
| 2013/0253405 | A1 | 9/2013 | Tu |
| 2017/0164831 | A1 | 6/2017 | Choo et al. |
| 2017/0215727 | A1 | 8/2017 | Chuck et al. |

(Continued)

FOREIGN PATENT DOCUMENTS

| | | |
|---|---|---|
| EP | 3082570 | 10/2018 |
| WO | 2020232015 | 11/2020 |

OTHER PUBLICATIONS

"The Solution: Eyemate®," IOP Implandata Ophthalmic Products GmbH, retrieved from the Internet Apr. 29, 2021 <https://www.implandata.com/EN/eyemate.html>, 2 pages.

(Continued)

*Primary Examiner* — Tse W Chen
*Assistant Examiner* — Joseph A Tombers
(74) *Attorney, Agent, or Firm* — Christensen O'Connor Johnson Kindness PLLC

(57) ABSTRACT

An intraocular pressure (IOP) measurement system. An ultrasound pressure sensor is implantable in an eye, wherein the sensor has a sealed cavity that changes shape as a function of IOP of the eye. An ultrasound transmitter emits an incident ultrasound beam. A receiver produces an output signal in response to receiving a reflected ultrasound beam. A spectrometer is configured to estimate the IOP of the eye based on processing the output signal of the receiver. Other aspects are also described and claimed.

24 Claims, 3 Drawing Sheets

(56) References Cited

U.S. PATENT DOCUMENTS

| | | |
|---|---|---|
| 2018/0085605 A1 | 3/2018 | Maharbiz et al. |
| 2018/0214025 A1 | 8/2018 | Homyk et al. |
| 2018/0344158 A1 | 12/2018 | Hastings et al. |
| 2019/0008400 A1 | 1/2019 | Richter et al. |
| 2019/0175015 A1 | 6/2019 | Adams et al. |

OTHER PUBLICATIONS

"Intacs Corneal Implants," Abot Intacs®—Intacs@ for Keratoconus, retrieved from the Internet Apr. 29, 2021 <kinacsforkeratoconus.com/about-intacs/>, 2 pages.

Weber, Marcus J., et al., "A Miniaturized Single-Transducer Implantable Pressure Sensor With Time-Multiplexed Ultrasonic Data and Power Links," IEEE Journal of Solid-State Circuits, vol. 53, No. 4, Apr. 2018, pp. 1089-1101.

Lee, Hee Su, et al., "An Intraocular Pressure Measurement Technique Based on Acoustic Radiation Force Using an Ultrasound Transducer: A Feasability Study," Sensors 2021, 21, 1857, 13 pages.

Phan, Alex, et al., "Development of an Intraocular Pressure Measurement System," UC San Diego, 2018, 1 page.

Chen, Po-Jui, et al., "Implantable micromechanical parylene-based pressure sensors for unpowered intraocular pressure sensing," Journal of Micromechanics and Microengineering, 17 (2007), Aug. 31, 2007, pp. 1931-1938.

Lin, Keng-Min, et al., "Introcular Pressure Sensors: New Approaches for Real-Time Intraocular Pressure Measurement Using a Purely Microfluidic Chip," 16th International Conference on Miniaturized Systems for Chemistry and Life Sciences, Oct. 28-Nov. 1, 2012, pp. 731-733.

Phan, Alex, et al., "Development of an Optical-Based Intraocular Pressure Sensor," UC San Diego, 2017, 1 page.

Edwards, Ed, "Common Types of Pressure Sensors," Types of Pressure Sensor—A Guide, retrieved from the Internet Apr. 26, 2021 <https://www.thomasnet.com/articles/instruments-controls/pressure-sensors/>, 8 pages.

Ou, MD, Yvonne, "How is Eye Pressure Measured?" BrightFocus@ Foundation, <https://www.brightfocus.org/glaucoma/article/how-eye-pressure-measured>, May 14, 2018, 5 pages.

Choritz, Lars, et al., "Telemetric Measurement of Intraocular Pressure via an Implantable Pressure Sensor—12-Month Results from the ARGOS-02 Trial," American Journal of Ophthalmology, vol. 209, Jan. 2020, pp. 187-196.

Lee, Jeong Oen, et al., "A microscale optical implant for continuous in vivo monitoring of intraocular pressure," Microsystems & Nanoengineering (2017) 3, 17057, 9 pages.

International Search Report and Written Opinion for International Application No. PCT/US2020/032510 mailed Jul. 30, 2020, 10 pages.

International Search Report and Written Opinion for International Application No. PCT/US2022/031634 mailed Sep. 14, 2022, 18 pages.

International Search Report and Written Opinion for International Application No. PCT/US2022/031617 mailed Sep. 14, 2022, 19 pages.

Phan, Alex, et al., "A Wireless Handheld Pressure Measurement System for In Vivo Monitoring of Intraocular Pressure in Rabbits," IEEE Transactions on Biomedical Engineering, vol. 67, No. 3, Mar. 2020, pp. 931-937.

Phan, Alex, et al., "Optical Intraocular Pressure Measurement System for Glaucoma Management," 2017 IEEE Healthcare Innovations and Point of Care Technologies, Nov. 6, 2017, pp. 188-191.

Phan, Alex, et al., "Design of an Optical Pressure Measurement System for Intraocular Pressure Monitoring," IEEE Sensors Journal, vol. 18, No. 1, Jan. 1, 2018, pp. 61-68.

Phan, Alex, et al., "A Compact Optical Pressure Measurement System for Acquiring Intraocular Pressure and Ocular Pulse," 2020 42nd Annual International Conference of the IEEE Engineering in Medicine & Biology Society (EMBC), Jul. 20, 2020, pp. 4212-4216.

International Preliminary Report on Patentability received for PCT Patent Application No. PCT/US2022/031634, mailed on Dec. 14, 2023, 10 pages.

* cited by examiner

ULTRASOUND INTRAOCULAR PRESSURE SENSOR IN SCLERA OR IN CORNEA

This patent application claims the benefit of the earlier filing date of U.S. provisional application No. 63/195,530 filed Jun. 1, 2021.

FIELD

The subject matter of this disclosure relates to techniques for measuring intraocular pressure in human eyes. Such techniques are useful for treating eye diseases including glaucoma, but are not limited to use with the treatment of eye disease.

BACKGROUND

Intraocular pressure (IOP) refers to the pressure of a fluid referred to as the aqueous humor inside the eye. The pressure is normally regulated by changes in the volume of the aqueous humor, but some individuals suffer from disorders, such as glaucoma, that cause chronic heightened IOP. Over time, heightened IOP can cause damage to the eye's optical nerve, leading to loss of vision. Presently, treatment of glaucoma mainly involves periodically administering pharmaceutical agents to the eye to decrease IOP. These drugs can be delivered, for example, by injection or eye drops. However, effective treatment of glaucoma requires adherence to dosage schedules and a knowledge of the patient's IOP. The more current or recent the measurement is, the more relevant it will be and hence the more effective the resulting treatment can be. The IOP for a given patient can vary significantly based on time of day, exercise, how recently a medication was taken, and other factors. Typically, IOP measurements are performed in a doctor's office and often no more once or twice per year. These infrequent measurements are less able to account for variation in the patient's IOP, and may become stale due to the length of time between them. This means that any given measurement is subject to uncertainty, so it may take several IOP measurements over time to have confidence of the health of the patient's eye.

Typically, the IOP is measured using a tonometer which is a device that is outside the eye and that does not require a sensor within the eye. Contact tonometry is performed in a clinical setting, and the procedure requires numbing of the patient's eye, resulting in both inconvenience and discomfort. Noncontact tonometry involves directing a puff or jet of air at the patient's eye and measuring the resulting deflection of the eye. However, this requires a bulky and power hungry pump arrangement that may not be practical for home use, and is not as accurate as noncontact tonometry.

SUMMARY

A minimally invasive, passive ultrasound sensor is implanted in the cornea or sclera of a person's eye, and is used to measure the IOP of the eye. To do so, a reader (an electronic device which may be portable, battery powered, and held by the person themselves) is aligned with the eye, and an ultrasound beam is emitted by an ultrasound transmitter inside the reader. The beam enters the cornea or sclera where it impinges upon the sensor and is reflected by the sensor, towards a receiver in the reader. The reflection changes as it follows the changing IOP of the eye for example over the course of a day. The sensor is passive in that it does not have a source of stored power that is used to transmit a signal containing information about the IOP. Instead, a part of the sensor that is reflecting the incident beam will bend or compress, as a function of the nearby IOP, resulting in the reflection changing accordingly. An estimate of the IOP is then determined by for example digitally processing an electrical output signal of the receiver (that is responsive to the reflection from the sensor.)

As the sensor is passive, it can be made small and thin so as to be implanted into the cornea in a minimally invasive manner, more easily and with less risk of complications as compared to implant locations that are further inside the eye. In another aspect, since the sensor operates in the ultrasound region, it may not need incident light for operation and as such could be implanted in a more hidden region of the eye (that is outside the visual path of the eye) such as the sclera. In one aspect, the sensor and the reader together are part of a consumer-focused solution that enables more frequent IOP measurements to be made by the patient at home, which are important for monitoring the progression of glaucoma and the effectiveness of any treatments.

The above summary does not include an exhaustive list of all aspects of the present disclosure. It is contemplated that the disclosure includes all systems and methods that can be practiced from all suitable combinations of the various aspects summarized above, as well as those disclosed in the Detailed Description below and particularly pointed out in the Claims section. Such combinations may have particular advantages not specifically recited in the above summary.

BRIEF DESCRIPTION OF THE DRAWINGS

Several aspects of the disclosure here are illustrated by way of example and not by way of limitation in the figures of the accompanying drawings in which like references indicate similar elements. It should be noted that references to "an" or "one" aspect in this disclosure are not necessarily to the same aspect, and they mean at least one. Also, in the interest of conciseness and reducing the total number of figures, a given figure may be used to illustrate the features of more than one aspect of the disclosure, and not all elements in the figure may be required for a given aspect.

DETAILED DESCRIPTION

Several aspects of the disclosure with reference to the appended drawings are now explained. Whenever the shapes, relative positions and other aspects of the parts described are not explicitly defined, the scope of the invention is not limited only to the parts shown, which are meant merely for the purpose of illustration. Also, while numerous details are set forth, it is understood that some aspects of the disclosure may be practiced without these details. In other instances, well-known circuits, structures, and techniques have not been shown in detail so as not to obscure the understanding of this description.

Figure 1:
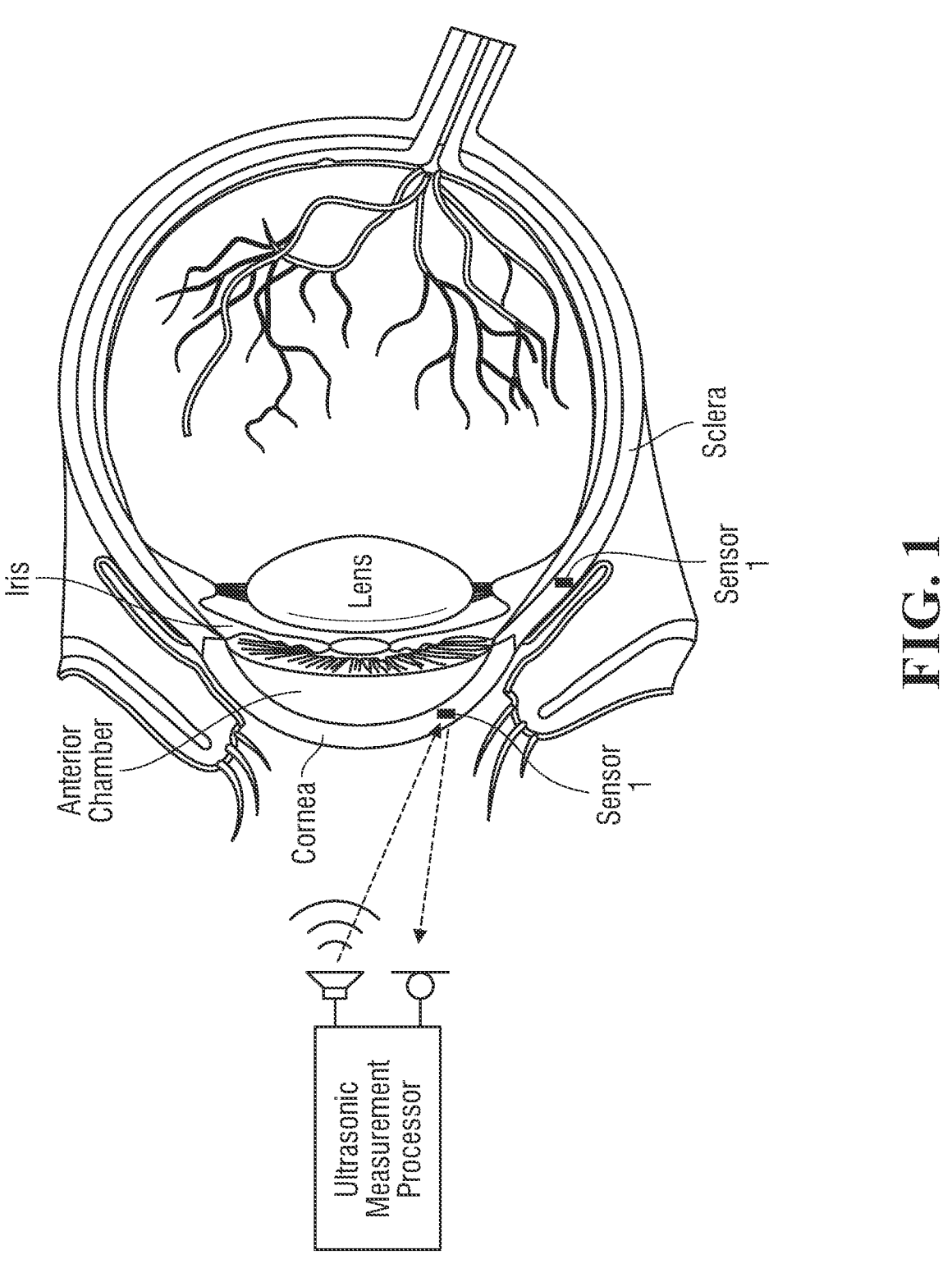
FIG. 1 shows an example of how to measure IOP using a passive, implanted ultrasound pressure sensor.

FIG. 1 shows an example of how to measure IOP using a passive ultrasound sensor 1 that has been implanted in the cornea or in the sclera. While the drawings in this disclosure may not be to scale, they do illustrate that the sensor 1 is small enough to be implanted into a typical cornea (which is about 0.5 mm thick), or into a typical sclera (which may also be about 0.5 mm thick.) The sensor 1 is passive in that it does not have a source of stored power that is used to transmit a signal containing information about the IOP. Instead, a part of the sensor 1 is designed to bend or compress or conform according to the IOP, and that part is also designed to reflect incident ultrasound energy. As a result, the sensor 1 changes how it reflects the ultrasound energy, as a function of the IOP at that moment. Thus, the reflection changes in that it follows the changing IOP, for example over the course of a day. As the sensor is passive, it can be made small and thin so as to be implanted into the cornea in a minimally invasive manner, more easily and with less risk of complications as compared to implant locations that are further inside the eye. In one aspect, the sensor is implantable in the cornea in its entirety as shown, so that it is entirely embedded in the cornea (there are no extensions or other pieces that extend beyond the cornea.) In another aspect, since the sensor operates in the ultrasound region, it may not need incident light for operation and as such could be implanted in a more hidden region of the eye (that is outside the visual path of the eye) such as the sclera. Here too, the sensor can be made sufficiently small so that it is entirely embedded in the sclera as shown (there are no extensions or other pieces attached to the sensor that extend beyond the cornea.)

Figure 3:
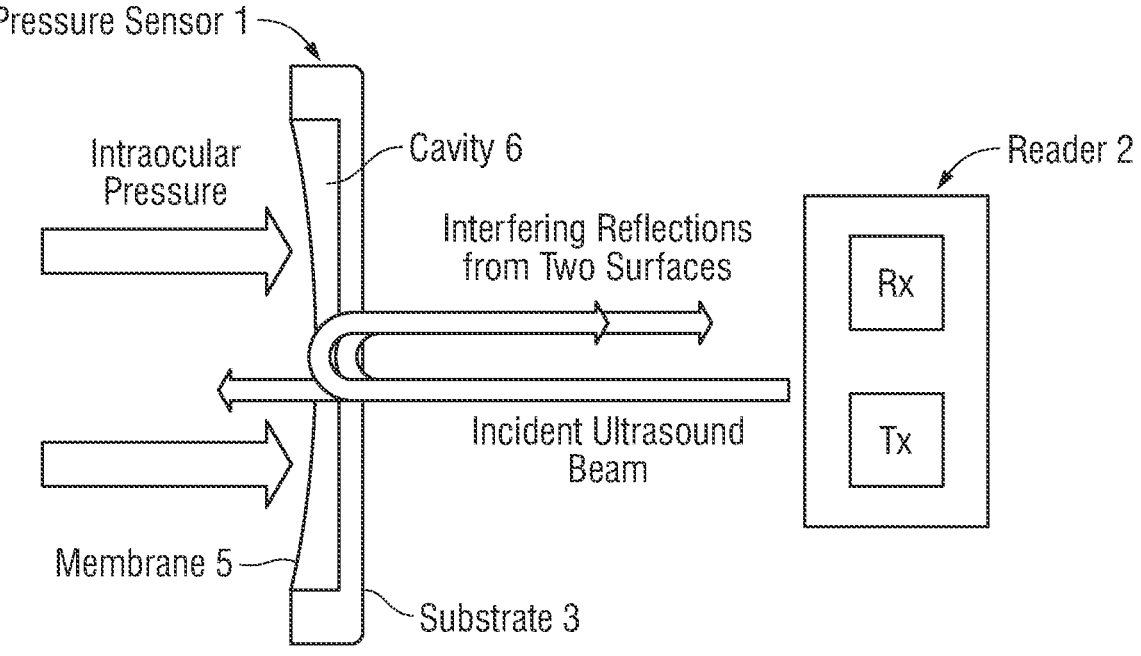
FIG. 3 shows an example ultrasound pressure sensor.

In one instance, referring now to the example shown in FIG. 3, the sensor 1 has a rigid substrate 3 to which a flexible membrane 5 (the terms rigid and flexible being relative to one another) is attached, so as to form a sealed cavity 6 that is bound by (or defined by) the internal faces of the substrate and the membrane. The membrane 5 may be made of one or more of the following materials: silica, zinc oxide, chrome, gold, silicon, germanium or any material that has a suitable acoustic index change from the surrounding tissue. The substrate 3 may be made of similar materials as well. The acoustic indices should be chosen to maximize the contrast of the interference that is due to reflections from two surfaces of the sensor 1. In one instance, a surface area of the sensor 1 on which an ultrasound beam is incident has dimensions that are smaller than one wavelength of the ultrasound beam within the tissue in which the sensor 1 implanted.

To make IOP measurements, a reader 2 contains an ultrasound transmitter (Tx) and an ultrasound receiver (Rx), both of which may be integrated within a housing of the reader. The reader is aligned with the eye so that a beam of incident ultrasound energy (waves) emitted by the transmitter impinges on the sensor 1, while reflections of those waves from the sensor 1 are detected by the receiver (as its output signal.) Note the term "beam" is used generically here, and does not require a beamforming transmitter array. The beam enters the cornea or sclera where it impinges (or is incident) upon the sensor 1, and is reflected by the sensor 1 towards the receiver. In the particular example of FIG. 3, the sensor 1 is oriented so that the incident beam impinges the rigid substrate 3 first, where some of the incident energy is reflected toward the receiver and some is transmitted into the cavity 6 where it is reflected (toward the receiver) off the membrane 5 as shown. An estimate of the IOP is then determined by an ultrasonic measurement processor, by digitally processing an electrical output signal of the receiver that is responsive to the interfering reflections from the two surfaces of the sensor 1. This is possible because the output signal of the receiver changes, in a detectable manner, as the sensor 1 bends or changes shape due to the changing IOP.

Another option for ultrasonic measurement is to consider that the stress induced to the membrane 5 (due to the changing IOP) changes the acoustic resonant frequency of the membrane, which changes the amplitude of the reflection. The frequency of the Tx could be swept to determine the resonant frequency, and thereby the pressure. In this case, only membrane 5 needs to have an acoustic reflection—the substrate 3 could be chosen to be acoustically transparent.

In the example of FIG. 3, the sealed cavity 6 is a gaseous volume that is made to be at a low enough pressure, for example on the order of the atmosphere (atm) or lower, that allows changes in the IOP to sufficiently bend or change the shape of the membrane 5 (via movement of the corneal or sclera tissue that surrounds the sensor 1 and that is caused by the changing IOP) so as to be detectable in the interfering reflections. In other words, the sealed cavity has a depth that varies as a function of the IOP of the eye in which it is implanted. The gaseous volume in the sealed cavity and the flexible membrane provide a frequency dependent, acoustic impedance to the incident ultrasound waves. The membrane changes shape as a function of IOP, and so changes the acoustic impedance presented to the incident ultrasound waves. Other ways of making the sensor 1 so that it provides a frequency dependent acoustic impedance to incident ultrasound energy are possible.

Based on knowledge of the transmitted waveform, the processor analyzes the signal from the receiver to interpret the reflections from the sensor 1 into an estimate of the IOP, e.g., in units of mmHg. The processor may look for a frequency dependent reflectivity characteristic in the receiver output signal, which can be correlated to how much the sensor 1 is being bent or compressed (by the IOP.) As such the processor may operate as a spectrometer (that performs a spectroscopy algorithm.)

Note that some or all of the digital signal processing that is performed upon the receiver output signal (by the ultrasound measurement process) may be performed by a digital processor which is inside the reader 2. That digital processor may alternatively be inside a companion device such as a smartphone which is wirelessly paired for data communication with the reader 2, and the reader 2 transmits a digital version of the receiver output signal to the companion device for processing. Some or all of the digital processing may be relegated to a cloud computing service.

A frequency of the transmitted ultrasound beam may be selected so as to increase the signal to ratio at the receiver output (which is detecting reflections from the implanted sensor 1.) In one aspect, the ultrasound beam is within the frequency range 2 MHz to 20 MHz. In one instance, the selected frequency may be one that results in low scattering (by skin and by the corneal or sclera tissue that surrounds the implanted sensor 1) over the first 100 microns of depth but then high scattering at greater depths (beyond the depth at which the sensor 1 is implanted.) In one aspect, the transmitter in is controlled so as to emit a variety of ultrasound frequencies. The transmitter may be configured to produce a linear chirp or a frequency sweep or other time dependent (time varying) ultrasound frequency waveform, acting to interrogate the sensor 1. In another aspect, the transmitter is configured to produce the interrogating, ultrasound beam as a noise-like waveform. In yet another aspect, the transmitter is configured to produce the interrogating ultrasound beam as a narrow band signal or tone that is coherent (has a stable and controlled phase), and the measurement processor is configured to perform coherent detection of the reflection in the receiver output signal. To improve signal to noise ratio (and reduce interference from other ultrasound sources), the transmitted ultrasound beam could be modulated with a code, which would be detectable when processing the output signal of the receiver.

If the sensor 1 is implanted further back than the cornea, such as in the sclera, then the reader may need to be configured to produce a wider or more spread out incident beam, or perhaps a more powerful incident beam, in order to more easily reach the sensor or in order to achieve a suitably high signal to noise ratio at the receiver's output. This will help loosen the requirement for aligning the transmitter-receiver to the sensor, thereby rendering a better user experience.

Figure 2:
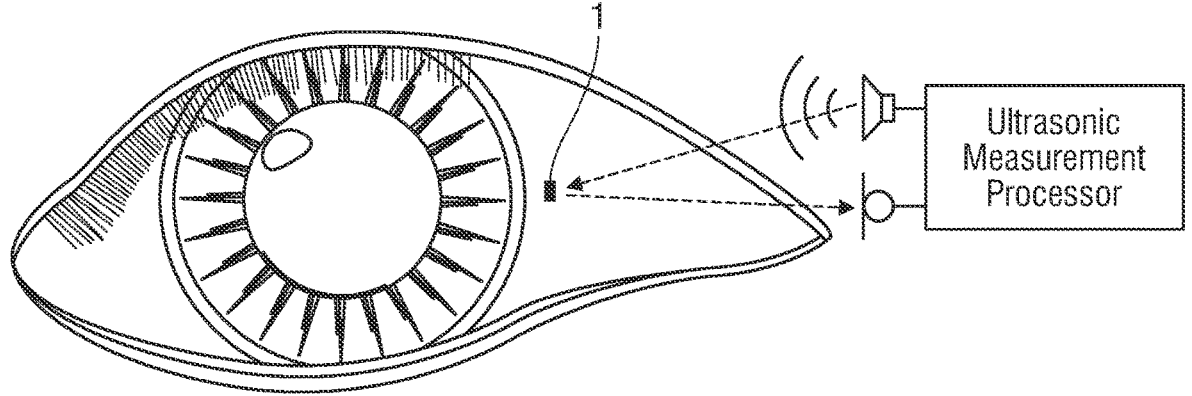
FIG. 2 illustrates another example of measuring IOP using a passive implanted ultrasound pressure sensor.

The reader 2 may be a handheld device, for example a consumer focused product that is to be held in the hand of the person, while being aimed at the front of their eye (in which the sensor 1 is implanted.) The external surface of the reader that is in the ultrasound energy path could be placed against an eyelid (of the person's closed eye whose IOP is being measured.) The person may be instructed to keep their eyes closed and look towards the reader, and keep a fixed gaze directly forward which may facilitate alignment of the sensor 1 with the transmitter-receiver pair. In another aspect, referring now to FIG. 2, the reader could be held to abut against the person's temple (rather than positioned directly in front of their eye), and the person may be instructed to keep a fixed gaze straight ahead. To improve the transfer of ultrasound energy, an impedance matching material such as a foam or gel may be attached or applied to the outside surface of the reader that comes into contact with the person's skin (on their eyelid or on their temple) and is in the transmitted and reflected ultrasound energy path. Alternatively, the reader could be placed elsewhere on the head of the person, or affixed to a bench or stand next to the person.

The reader 2 may have an acoustic lens that focuses the ultrasound beam being emitted by the transmitter. The transmitter may be an array of ultrasound emitters that is driven by a beamforming processor to emit a narrow or directional primary lobe. The receiver may be an array of ultrasound detectors whose output signals are processed into a beam pickup signal (by a beamforming algorithm.) The focused or narrowed beams may be combined with a scanning mechanism, either mechanical or, in the case of a beamforming array, a scanning array algorithm, that can be used to sweep an area where the sensor 1 is expected to be located so as to reduce the constraints on how the reader is to be held against the eye or positioned on the person's head.

Since the cornea and the sclera are not actually inside the eye (immersed in the aqueous humor), an IOP estimate that is determined using a pressure sensor implanted in the cornea or sclera is not as direct a measurement of the IOP as would be obtained using a sensor that is for example within the anterior chamber of the eye. As such, one or more parameters may need to be determined for example by a calibration procedure that is performed with the reader and the sensor as implanted. The parameter may account for the indirectness of the measurement. The parameter relates changes in IOP to corresponding changes in the cornea or sclera that cause the implanted sensor to bend or compress leading to the reflection of the incident beam that is detected by the receiver. The parameter's value may be different for each instance of the implanted sensor (in different eyes of the same person and in different persons) as it may also be a function of for example the depth (in the thickness direction) of the implant location in the cornea or sclera, or more generally the position of the implanted sensor. Such a parameter may be for instance a scaling factor or an additive offset that is applied by a digital processor to a reading of the output signal of the receiver. The parameter may alternatively be part of a more complex set of parameters that are applied to the receiver readings, for example by a machine learning model.

While certain aspects have been described and shown in the accompanying drawings, it is to be understood that such are merely illustrative of and not restrictive on the broad invention, and that the invention is not limited to the specific constructions and arrangements shown and described, since various other modifications may occur to those of ordinary skill in the art. For example, while FIG. 1 shows two instances of the sensor 1, one in the cornea and another in the sclera, it should be understood that either one of the sensors by itself may be sufficient to make the IOP measurement (in conjunction with the reader as explained above.) The description is thus to be regarded as illustrative instead of limiting.

What is claimed is:

1. An intraocular pressure (IOP) measurement system comprising:
   an ultrasound pressure sensor implantable in an eye, wherein the sensor has a sealed cavity that changes shape as a function of IOP of the eye, the sealed cavity defined by a membrane and a rigid substrate;
   an ultrasound transmitter configured to emit an incident ultrasound beam, the ultrasound pressure sensor being configured to be positioned in a manner that the incident ultrasound beam reaches the rigid substrate before the membrane;
   a receiver configured to produce an output signal determined based on interfering reflections of an ultrasound beam off the membrane and the rigid substrate; and
   a spectrometer configured to estimate the TOP of the eye based on processing the output signal of the receiver.

2. The system of claim 1 wherein the sensor is implantable in a cornea of the eye.

3. The system of claim 2 wherein the sensor is implantable in the cornea in its entirety so that it is entirely embedded in the cornea.

4. The system of claim 1 wherein the sensor is implantable in a sclera of the eye.

5. The system of claim 4 wherein the sensor is implantable in the sclera in its entirety so that it is entirely embedded in the sclera.

6. The system of claim 1 wherein the membrane is a flexible membrane which is attached to the rigid substrate.

7. The system of claim 6 wherein the membrane and cavity provide a frequency dependent, acoustic impedance to the incident ultrasound beam, that changes as a function of the IOP.

8. The system of claim 6 wherein the sealed cavity is a gaseous cavity.

9. The system of claim 6 wherein the rigid substrate is at least partially transparent to the incident ultrasound beam while the membrane is reflective to the incident ultrasound beam thereby producing the interfering reflections.

10. The system of claim 1 wherein the ultrasound transmitter and the receiver are integrated within a single housing of a reader.

11. The system of claim 10 wherein the reader is a handheld device, and the spectrometer comprises a digital processor that is outside of the handheld device.

12. A method for measuring IOP of an eye, the method comprising:
   emitting an ultrasound beam toward a pressure sensor, which is implanted in a cornea or a sclera of the eye, the pressure sensor being configured to be positioned in a manner that the ultrasound beam reaches a rigid substrate of the pressure sensor before a membrane of the pressure sensor;

detecting, as an output signal, interfering reflections of the ultrasound beam from the membrane and the rigid substrate; and processing the output signal to compute an estimate of the TOP of the eye.

13. The method of claim 12 wherein processing the output signal comprises performing a spectroscopy algorithm.

14. The method of claim 13 wherein the sensor is implanted in the cornea.

15. The method of claim 14 wherein the sensor is implanted in the cornea in its entirety so that it is entirely embedded in the cornea.

16. The method of claim 12 wherein the sensor is implanted in the sclera.

17. The method of claim 16 wherein the sensor is implanted in the sclera in its entirety so that it is entirely embedded in the sclera.

18. The method of claim 12 wherein processing the output signal comprises computing an estimate of frequency dependent, acoustic impedance presented to the ultrasound beam, that changes as a function of the IOP.

19. The method of claim 12 wherein the membrane is a flexible membrane which is attached to the rigid substrate to define a sealed cavity.

20. The method of claim 19 wherein the sealed cavity is a gaseous cavity.

21. The method of claim 12 wherein the rigid substrate is at least partially transparent, and the membrane is reflective to the ultrasound beam.

22. The method of claim 12 wherein emitting, detecting, and processing are performed by electronics that are integrated within a single housing of a reader.

23. The method of claim 22 wherein the reader is a handheld device, and the method further comprises transmitting a digital version of the output signal to a digital processor that is outside of the handheld device and that performs the processing of the output signal to compute the estimate of the IOP of the eye.

24. A non-transitory processor-readable storage medium storing a plurality of processor-executable instructions for measuring IOP of an eye, the plurality of processor-executable instructions being executed by a processor to perform operations comprising:

actuating an ultrasound transmitter to emit an ultrasound beam toward the eye;

detecting, as an output signal, interfering reflections of the ultrasound beam from a membrane and a rigid substrate of a pressure sensor that is implanted in a cornea or sclera of the eye, the pressure sensor being configured to be positioned in a manner that the ultrasound beam reaches the rigid substrate before the membrane; and processing the output signal to compute an estimate of the TOP of the eye.

* * * * *